United States Patent [19]

Duffett

[11] Patent Number: Plant 5,733

[45] Date of Patent: Apr. 29, 1986

[54] CHRYSANTHEMUM PLANT NAMED QUEST

[75] Inventor: William E. Duffett, Salinas, Calif.

[73] Assignee: Yoder Brothers, Inc., Barberton, Ohio

[21] Appl. No.: 644,261

[22] Filed: Aug. 27, 1984

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Quest characterized as to uniqueness by the combined characteristics of flat capitulum form, decorative capitulum type, yellow ray floret color, diameter across face of capitulum ranging from 9 to 10 cm. at maturity, uniform eight week flowering response, medium plant height, spreading branching pattern, tolerance of both low winter 13° C. minimum and high summer 24° C. night to 38° C. day temperatures for bud initiation and flower development, and its tolerance of very low winter light environment with 15° C. minimum temperature.

3 Drawing Figures

The present invention comprises a new and distinct cultivar of *Chrysanthemum morifolium*, Ramat., named Quest.

Quest is a product of a planned breeding program which had the objective of creating new chrysanthemum cultivars for pinched disbud pot mum programs having decorative capitulum type, yellow floret color, eight week flowering response and the ability to produce commercially acceptable quality in year round programs. Such traits in combination were not present or required improvements in previously available commercial cultivars.

Quest was originated from a cross made in a controlled breeding program in Salinas, Calif. in 1980. The female parent was identified as 75200070, an unnamed yellow decorative seedling originated by the present inventor from a cross of two unnamed seedlings. The male parent of Quest was identified as 79990002, an unnamed yellow decorative originated from a cross between two unnamed seedlings.

Quest was discovered and selected as one flowering plant within the progeny of the stated cross by William E. Duffett in October 1981 in a controlled environment in Salinas, Calif.

The first act of asexual reproduction of Quest was accomplished when vegetative cuttings were taken from the initial selection in December 1981 in a controlled environment in Salinas, Calif. by a technician working under formulations established and supervised by William E. Duffett. Horticultural examination of selected units initiated March 1982 has demonstrated that the combination of characteristics as herein disclosed for Quest are firmly fixed and are retained through successive generations of asexual reproduction.

Quest has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Quest which in combination distinguish this chrysanthemum as a new and distinct cultivar:

1. Flat capitulum form.
2. Decorative capitulum type.
3. Yellow ray floret color.
4. Diameter across face of capitulum ranging from 9 to 10 cm. at maturity.
5. Uniform eight week photoperiodic flowering response to short days.
6. Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots).
7. Spreading branching pattern.
8. Tolerance of low winter 13° C. minimum temperature.
9. Tolerance of high summer 24° C. night and 38° C. day temperatures.
10. Tolerance of very low winter light with 15° C. minimum temperature.

The accompanying photographic drawings depict typical leaf and inflorescence characteristics of Quest. Sheet 1 is a color photograph of a plant of Quest grown as a pinched, disbud pot mum, with colors being as accurate as possible with renditions of this type. Sheet 2 is a black and white photograph of three views of the inflorescence of Quest. Sheet 3 shows the upper and under surfaces of leaves of Quest in three stages of growth (mature, intermediate, immature).

Of the many commercial cultivars known to the present inventor, the most similar in comparison to Quest is Sunny Mandalay, disclosed in U.S. Plant Pat. No. 3,231. Reference is made to attached Chart A which compares certain characteristics of Quest to those same characteristics of Sunny Mandalay. Traits similar in both cultivars are capitulum form, type and diameter. Plant height and branching pattern are nearly equal. Quest has a more clear yellow ray floret color and its tolerance of high and low temperatures results in more rapid response and shorter crop time.

In the following description, color references are made to The Royal Horticultural Society Colour Chart. The color values were determined between 10:45 A.M.

and 11:00 A.M. on Mar. 6, 1984 under 380 foot-candle light intensity at Salinas, Calif.

Classification:

*Botanical.*—*Chrysanthemum morifolium,* Ramat. cv QUEST.

*Commercial.*—Decorative disbud pot mum.

I. INFLORESCENCE

A. Capitulum:

*Form.*—Flat.

*Type.*—Decorative.

*Diameter across face.*—9 to 10 cm.

B. Corolla of ray florets:

*Color (general tonality from a distance of three meters).*—Yellow.

*Color (upper surface).*—9A and 12A.

*Color (under surface).*—9B.

*Shape.*—Long, broad, pointed tip.

C. Corolla of disc florets:

*Color (mature).*—154A.

*Color (immature).*2B.

D. Reproductive organs:

*Androecium.*—present disc florets only; scant pollen.

*Gynoecium.*—Present both ray and disc florets.

II. PLANT

A. General appearance:

*Height.*—Medium.

*Branching pattern.*—Spreading.

B. Foliage:

*Color (upper surface).*—137A, B.

*Color (under surface).*—138A.

*Shape.*—Narrow, shallow lobes. Shallow with moderate and pointed serration.

CHART A

COMPARISON OF QUEST AND SUNNY MANDALAY

| CULTIVAR | RAY FLORET COLOR | CAPITULUM FORM AND TYPE | BRANCHING PATTERN |
|---|---|---|---|
| QUEST | YELLOW | FLAT DECORATIVE | SPREADING |
| SUNNY MANDALAY | YELLOW TINGED ORANGE | FLAT DECORATIVE | SPREADING |

| CULTIVAR | DIAMETER ACROSS FACE OF CAPITULUM | PLANT HEIGHT | FLOWERING RESPONSE PERIOD | TEMPERATURE TOLERANCE |
|---|---|---|---|---|
| QUEST | 9 to 10 cm. | MEDIUM | EIGHT WEEKS | LOW - 13° C. HIGH - 24° C. NIGHT TO 38° C. DAY |
| SUNNY MANDALAY | 9.5 to 10.5 cm. | MEDIUM | NINE WEEKS | LOW - POOR HIGH - POOR |

COMPARISONS MADE OF PLANTS GROWN AS PINCHED DISBUDDED POT MUMS IN SALINAS, CALIFORNIA AND LEAMINGTON, ONTARIO, CANADA

I claim:

1. A new and distinct cultivar of *Chrysanthemum morifolium,* Ramat., plant named Quest, as described and illustrated, and particularly characterized as to uniqueness by the combined characteristics of flat capitulum form; decorative capitulum type; yellow ray floret color; diameter across face of capitulum ranging from 9 to 10 cm. at maturity; uniform eight week flowering response; medium plant height; spreading branching pattern; tolerance of both low winter 13° C. minimum and high summer 24° C. night to 38° C. day temperatures for bud initiation and flower development, and its tolerance of very low winter light environment with 15° C. minimum temperature.

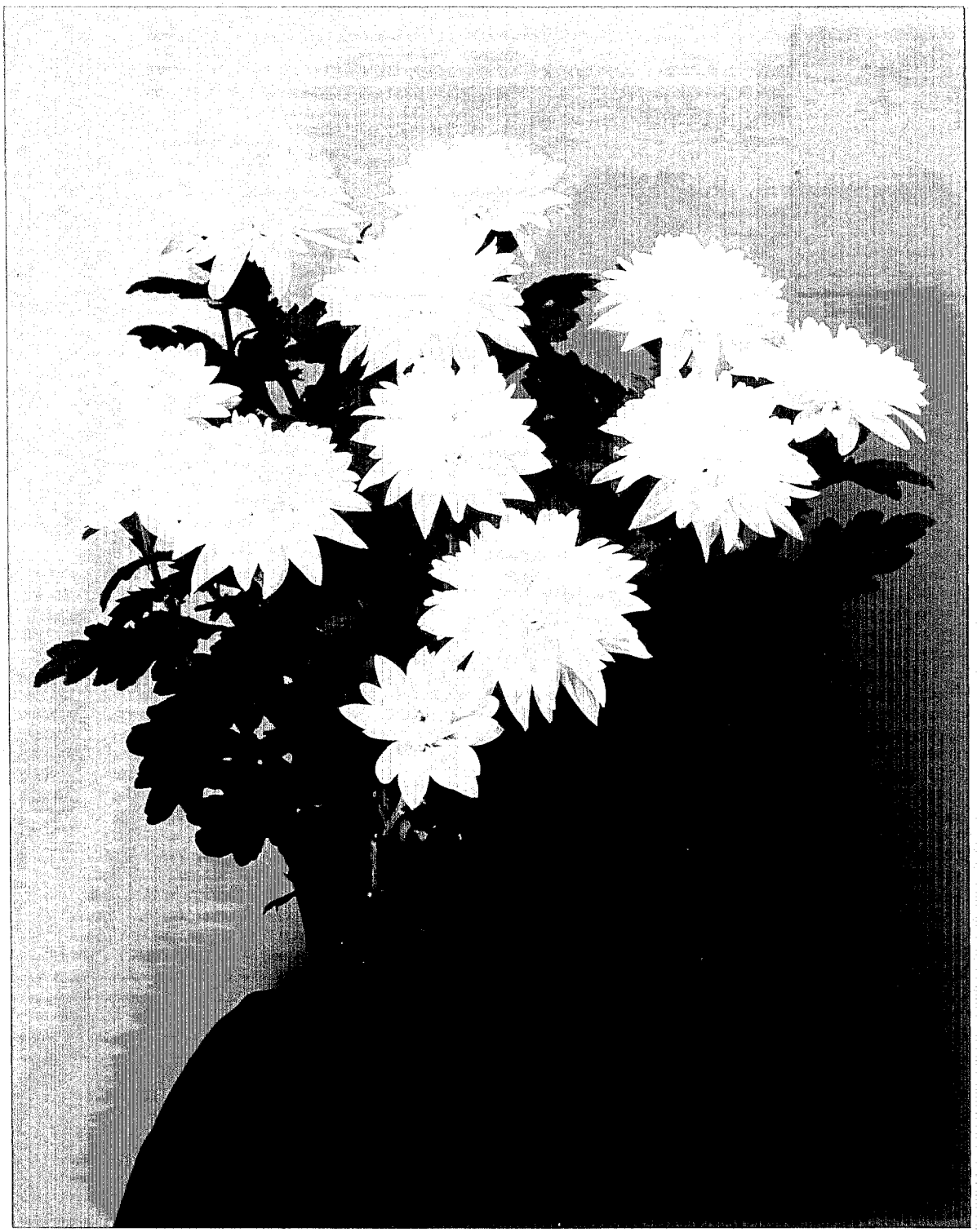

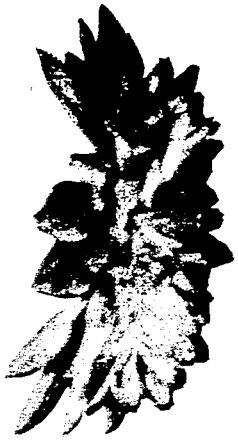
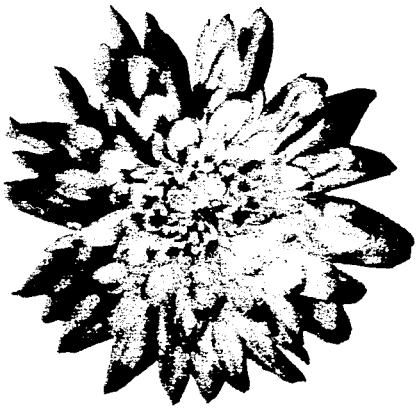
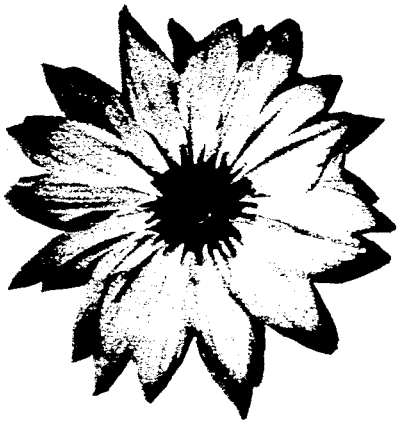

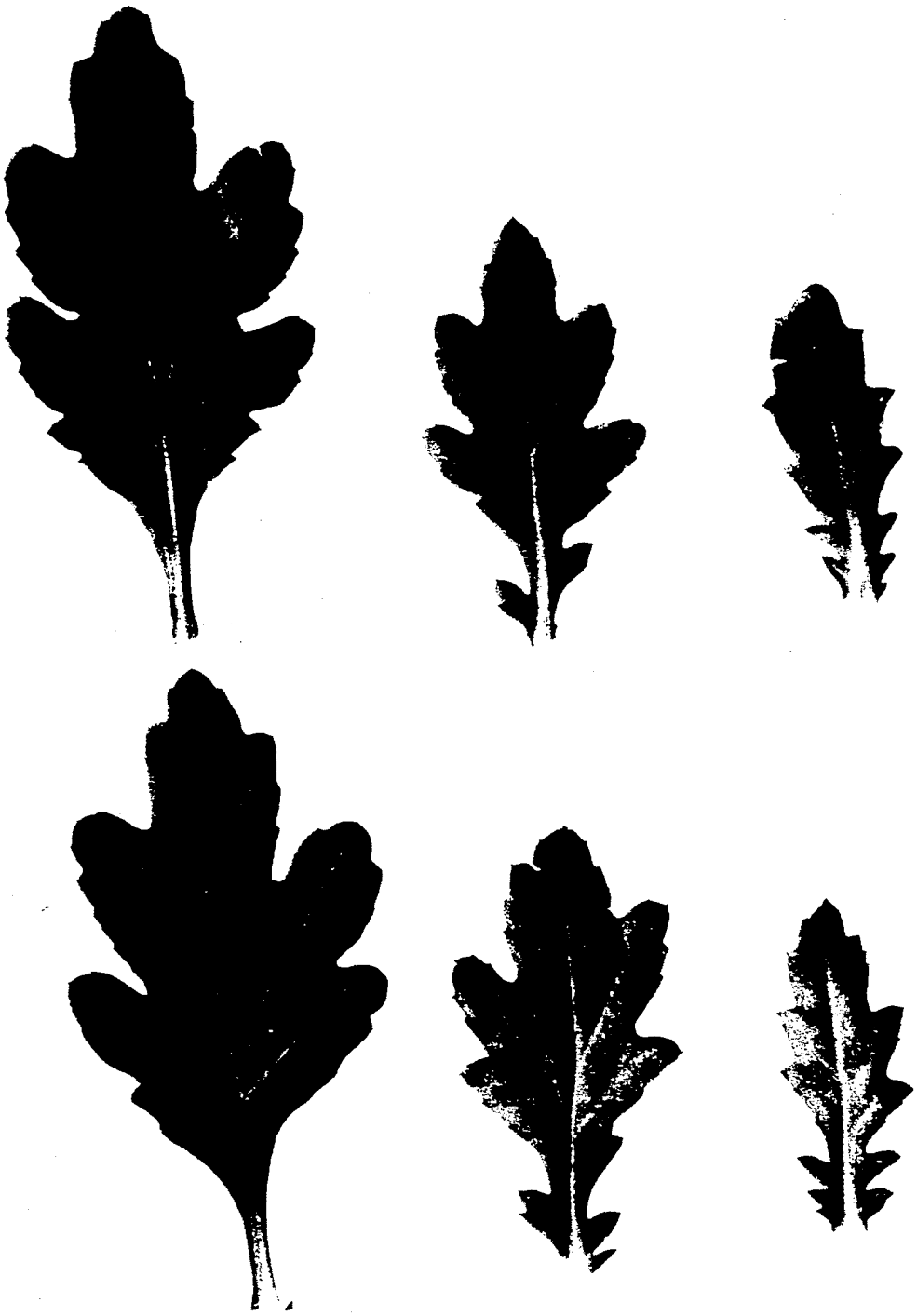

* * * * *